(12) United States Patent
Binkowski

(10) Patent No.: US 11,096,587 B2
(45) Date of Patent: Aug. 24, 2021

(54) INTRA-ORAL SCANNING DEVICE, METHOD OF OPERATING SUCH A DEVICE AND SCANNER SYSTEM

(71) Applicant: N-LAB MARCIN BINKOWSKI, Katowice (PL)

(72) Inventor: Marcin Binkowski, Katowice (PL)

(73) Assignee: DEVENTIV SP. Z O.O., Katowice (PL)

( * ) Notice: Subject to any disclaimer, the term of this patent is extended or adjusted under 35 U.S.C. 154(b) by 165 days.

(21) Appl. No.: 16/492,335

(22) PCT Filed: Mar. 8, 2018

(86) PCT No.: PCT/EP2018/055762
§ 371 (c)(1),
(2) Date: Sep. 9, 2019

(87) PCT Pub. No.: WO2018/162641
PCT Pub. Date: Sep. 13, 2018

(65) Prior Publication Data
US 2021/0127979 A1  May 6, 2021

(30) Foreign Application Priority Data
Mar. 9, 2017  (CH) .................................... 00283/17

(51) Int. Cl.
*A62B 1/04* (2006.01)
*A61B 5/00* (2006.01)
(Continued)

(52) U.S. Cl.
CPC .............. *A61B 5/0088* (2013.01); *A61B 1/24* (2013.01); *A61B 5/0062* (2013.01); *A61C 7/002* (2013.01);
(Continued)

(58) Field of Classification Search
CPC ....... A61B 5/0088; A61B 5/0062; A61B 1/24; A61C 13/0004; A61C 9/0053; A61C 19/05; A61C 7/002
(Continued)

(56) References Cited

U.S. PATENT DOCUMENTS 6,364,660 B1   4/2002  Durbin et al.
8,989,567 B1   3/2015  Pulido et al.
(Continued)

FOREIGN PATENT DOCUMENTS

DE   102014205784 A1   10/2015
WO     2015/178962 A1   11/2015

OTHER PUBLICATIONS

International Search Report and Written Opinion dated Jun. 15, 2018 in corresponding International Patent Application No. PCT/EP2018/055762.

*Primary Examiner* — Robert Chevalier
(74) *Attorney, Agent, or Firm* — Medler Ferro Woodhouse & Mills PLLC

(57) ABSTRACT

An intra-oral scanning device includes a main part having a first mount structure, a scanning arm having at least one signal collector, a drive mechanism connected to the scanning arm to move a head portion of the scanning arm, and a mouthpiece positionable in an oral cavity. The mouthpiece has a hollow interior, an opening to access the hollow interior and a second mount structure. The scanning arm extends into the hollow interior when the first mount structure is connected to the second mount structure. The scanning arm is mounted to a pivot manipulator of the drive mechanism such that an axis of rotation of the pivot manipulator is essentially perpendicular to a longitudinal axis of the scanning arm. The scanning arm is mounted to a linear manipulator of the drive mechanism such that a distance
(Continued)

between the pivot manipulator and the head portion of the scanning arm is modifiable.

20 Claims, 7 Drawing Sheets

(51) Int. Cl.
    *A61C 13/00*    (2006.01)
    *A61C 9/00*    (2006.01)
    *A61C 19/05*    (2006.01)
    *A61C 7/00*    (2006.01)
    *A61B 1/24*    (2006.01)
    *H04N 7/18*    (2006.01)

(52) U.S. Cl.
    CPC ........ *A61C 9/0053* (2013.01); *A61C 13/0004* (2013.01); *A61C 19/05* (2013.01)

(58) Field of Classification Search
    USPC .................................. 348/66, 61, 64, 65, 77
    See application file for complete search history.

(56) References Cited

U.S. PATENT DOCUMENTS

| | | | |
|---|---|---|---|
| 2005/0155601 A1* | 7/2005 | Steiner .............. | A61M 15/0051 |
| | | | 128/200.23 |
| 2006/0154198 A1 | 7/2006 | Durbin et al. | |
| 2016/0279354 A1* | 9/2016 | de Kruijf .......... | A61M 15/0086 |
| 2017/0128173 A1 | 5/2017 | Berner et al. | |

* cited by examiner

INTRA-ORAL SCANNING DEVICE, METHOD OF OPERATING SUCH A DEVICE AND SCANNER SYSTEM

TECHNICAL FIELD

The present invention relates to an intra-oral scanning device according to the preamble of independent claim 1 and more particularly to a scanner system and a method of operating an intra-oral scanning device.

Such intra-oral scanning devices comprise (i) a main part having a first mount structure, (ii) a scanning arm having a head portion equipped with at least one scanning sensor, wherein the scanning arm is mounted to the main part and is arrangeable to protrude from the main part, (iii) a drive mechanism connected to the scanning arm to move the head portion of the scanning arm along an oral cavity of the patient, and (iv) a mouthpiece for being positioned in the oral cavity of a patient, having a hollow interior, an opening to access the hollow interior and a second mount structure corresponding to the first mount structure of the main part, wherein the scanning arm extends into the hollow interior of the mouthpiece when the first mount structure of the main part is connected to the second mount structure of the mouthpiece. Such devices can be used for providing data or images about an oral cavity of a patient. Such data can be desired for generating a model of the oral cavity or for developing a diagnosis and treatment in a dental therapeutic application.

BACKGROUND ART

Widespread methods for generating electronic images of oral cavities or of jaws are based on a tray filled with alginate, which is disposed into the mouth of a patient to make an impression. In a following step, the gypsum model is casted by means of the impression. Moreover, scanning the model by means of a table scanner based on either images or more likely structural light is often carried out. Inconveniences involved with such systems comprise that it is not easy to handle the materials which may stress the patient, cause low precision, introduce contaminations into the material used for the impression which may also be transferred to the gypsum model, that the model takes physical space and may be comparably costly and that the models need to be stored which requires space in a shelf at the dental office or lab.

A more advanced solution for providing images or models of oral cavities or jaws are hand-held scanning apparatuses, which are growingly used in dental clinics. Such apparatuses usually include a device, which is moved by the operator during scanning. Generally, all such apparatuses are based on the same concept of manual operation which requires the operator to spend time for moving the device along the arch of the teeth. They, typically have plural disadvantages such as a comparably low reproducibility, a comparably low accuracy and the like. These disadvantages lead many dentists to select traditional impression tray for generating images and models of jaws or oral cavities rather than using scanning techniques.

Furthermore, automatic oral scanners are getting more and more subjected in research and development. General purpose of such a scanner is to make the scanning process independent from a human operator, faster, more reproducible and more accurate. However, most known solutions are still suffering with technical design drawback such as either not being optimal motorised or lacking the ability to be adjusted to the patient's given situation.

An example of a comparably advanced intra-oral scanning device is described in WO 2015/178962 A1. This device comprises a housing body and a hollow mouthpiece of a transparent material. The mouthpiece is connectable to the housing body. The housing body houses a chassis comprising an arm to which a scanning head equipped with plural scanning sensors is mounted. When the mouthpiece is connected to the housing body, the arm extends to the mouthpiece such that the scanning head is located in the interior of the mouthpiece. A driving mechanism linearly displaces the arm for moving the scanning head inside the mouthpiece. In operation, a patient introduces the mouthpiece inside his mouth and the arm is displaced such that the scanning head is moved along the teeth of either the upper or the lower jaw of the patient. Even though the linear driving mechanism allows the arm to be displaced comparably precisely it requires the mouthpiece to have a wide opening in order that the arm can be displaced in the full range of the mouthpiece. Since on the other hand the human mouth is rounded at its front or mesial end, arranging the mouthpiece inside the oral cavity is comparably inconvenient. This leads the patient to perform compensation movements that may affect the accuracy of the scanning process.

Therefore, there is a need for a device, system or method allowing for a convenient, automatic and accurate scanning of an oral cavity of a patient.

DISCLOSURE OF THE INVENTION

According to the invention this need is settled by an intra-oral scanning device as it is defined by the features of independent claim 1, by a scanner system as it is defined by independent claim 23 and by a method of operating an intra-oral scanning device as it is defined by the features of independent claim 28. Preferred embodiments are subject of the dependent claims.

In particular, the invention deals with an intra-oral scanning device, which comprises a main part, a scanning arm, a drive mechanism and a mouthpiece. The main part has a first mount structure. The scanning arm has a head portion equipped with at least one signal collector. The scanning arm is mounted to the main part and is arrangeable to protrude from the main part. The term "protrude" in this connection can relate to stand off or project off or extend from the main part. The drive mechanism is connected to the scanning arm to move the head portion of the scanning arm along an oral cavity of a patient. The patient can be a living or dead human or animal being as well as a model of those, an archaeological artefact or the like. The mouthpiece is arranged to be positioned in the oral cavity of a patient. It has a hollow interior, an opening to access the hollow interior and a second mount structure corresponding to the first mount structure of the main part. The scanning arm extends into the hollow interior of the mouthpiece when the first mount structure of the main part is connected to the second mount structure of the mouthpiece.

The term "arm" as used herein relates to an elongated or elongatable one piece or multi piece structure. It can comprise or be a bar, a rail, a rod, a post or a similar element. It can further be telescopic or similarly elongatable. Also it can be equipped with one or plural joints or curves or the like. The head portion of the scanning arm can be integral with the scanning arm in one single piece or it can be mounted to a bar or similar element of the scanning arm. The scanning arm can particularly be shaped and embodied to guide the at least one signal collector of its head portion.

The drive mechanism has a pivot manipulator and a linear manipulator. The scanning arm is mounted to the pivot manipulator such that an axis of rotation of the pivot manipulator is essentially perpendicular to a longitudinal axis of the scanning arm. The scanning arm is mounted to the linear manipulator such that a distance between the pivot manipulator and the head portion of the scanning arm is modifiable.

The intra-oral scanning device can particularly be suitable for performing a dental scan.

The term "signal" as used herein can relate to light signal preferably of specific wavelengths, an ultrasound signal, an infrared signal, a monochromatic light signal, a fluorescence signal or the like.

The at least one signal collector can be an optics directing image information to a target or sensing unit. Such optics can comprise or be a mirror, a lens, a collimator, a reflector, a refractor or a similar optical or non optical element. The signal can be transferred by transfer by any optical channel like in endoscopy, a cable, a fibre or via the air from such a signal collector to the sensing unit.

Preferably, the at least one signal collector comprises a scanning sensor or is at least one scanning sensor. The scanning sensors can be or comprise visible light or infrared cameras or the like. Suitable scanning sensors can be or comprise active-pixel sensors such as complementary metal-oxide-semiconductor (CMOS) sensors or charge-coupled device (CCD) image sensors, stereo cameras, ultrasound sensors, infrared sensors, infra-waves sensors, fluorescence sensors, acoustic sensors, spectroscopic sensors, dual cameras, array cameras, any combinations thereof or the like.

The provision of the pivot manipulator and the linear manipulator allows for moving the head portion of the scanning arm in a polar coordinate system. Like this, the scanning head can precisely move inside the mouthpiece. In particular, such drive mechanism allows for accurately moving the head portion or scanning head essentially over the complete interior of the mouthpiece. Additionally, moving the scanning arm in the polar coordinate system allows the opening of the mouthpiece to be comparably small. This can particularly be true when the pivot manipulator is located comparably close to the opening. Like this, the mouthpiece can be shaped to properly suit into the mouth of the patient. Therefore, the intra-oral scanning device according to the invention allows for a convenient and accurate automated scanning of the oral cavity of a patient.

Preferably, the drive mechanism has a motor arrangement arranged to adapt the pivot manipulator and the linear manipulator in order to move the head portion of the scanning arm in the hollow interior of the mouthpiece. The motor arrangement can be equipped with one or plural motors such as a linear motor or a rotational motor or the like. Such a motor allows for automatically displacing the scanning arm such that its head portion can also be moved automatically. Additionally, the motor can also be used for tilting the head portion or the at least one signal collector as described below. Such a motor also can be precisely controlled, e.g., by an appropriate software running on a control unit.

Preferably, the mouthpiece is made of a disposable material. The term "disposable" in this connection relates to a material which one hand is comparably low-cost and on the other hand does not require any particular treatment when being littered. A possible disposable material is Poly(methyl methacrylate) (PMMA) or a similar plastic material. This embodiment allows for replacing the mouthpiece after use, which can increase the hygiene of the application. Alternatively, the mouthpiece can be made of a sterilizable material which can conveniently be reused.

Preferably, the mouthpiece has a top portion limiting or covering the hollow interior and arranged to be directed towards an upper jaw of the patient when the mouthpiece is positioned in the oral cavity of the patient, the top portion being made of a transparent material. The upper jaw can also be referred to as maxilla. Such a mouthpiece allows for efficiently scanning the maxilla.

Additionally or alternatively, the mouthpiece has a bottom portion limiting the hollow interior and arranged to be directed towards a lower jaw of the patient when the mouthpiece is positioned in the oral cavity of the patient, the bottom portion being made of a transparent material. The lower jaw can also be referred to as mandible. Such a mouthpiece allows for efficiently scanning the mandible eventually as well as the maxilla.

Thereby, the at least one signal collector preferably is arranged to simultaneously scan via the top portion of the mouthpiece and the bottom portion of the mouthpiece when the head portion of the scanning arm is arranged inside the hollow interior of the mouthpiece. Such embodiment allows for simultaneously scanning the maxilla and the mandible, which can make the overall scanning process more efficient.

Preferably, the scanning arm is exclusively movable by the pivot manipulator rotating the scanner arm about the axis of rotation and the linear manipulator moving the scanner arm along its longitudinal axis. Like this, the degrees of freedom can be fixed to the number required for scanning the oral cavity. This allows for efficiently implementing the intra-oral scanning device.

Preferably, the pivot manipulator of the drive mechanism is mounted to the main part and the linear manipulator of the drive mechanism is mounted to the pivot manipulator of the drive mechanism. This allows for efficiently mounting or assembling the drive mechanism and requiring comparably little space.

Preferably, the mouthpiece comprises a sideward and/or frontward extending wing portion arrangeable between a soft tissue of the patient and a jaw of the patient when the mouthpiece is positioned in the oral cavity of the patient. The soft tissue can particularly be a cheek, lips or both. Such a wing portion allows for generating a space between the cheek and/or lips and the jaw. Thus, also the outer buccal side and/or the front labial side of the jaw can be efficiently scanned. The wing portion can have a buccal section and a labial section such that together they can form an arch wing portion.

Preferably, the mouthpiece comprises a frontward extending shield portion arrangeable adjacent to the main body in front of the mouth of the patient when the mouthpiece is positioned in the oral cavity of the patient. Such a shield portion can protect the main part and the mechanics of the device from contaminations such as saliva or the like.

Preferably, the intra-oral scanning device comprises a data interface for transferring scanner data gathered via the at least one signal collector, wherein the data interface preferably is a wireless data interface. Such data interface allows for transferring the data to an evaluating and/or displaying device. The wireless data interface may be particularly advantageous since it allows for a free and unhindered movement of the device.

Thereby, the data interface preferably is arranged to transfer data gathered by the at least one signal collector to a remote computer or a remote display. The remote computer can be a server or other computer in the cloud. Thus, the intra-oral scanning device can be embodied to directly providing the gathered data into the cloud or the Internet. The remote display can be a display distant from the intra-oral scanning device. It can also be associated to a computer to which the gathered data is transferred. Any such computer can be used to analyze or evaluate the gathered data. For example, it can reconstruct a three dimensional model of the oral cavity or sections thereof from the gathered data such as gathered images.

Preferably, the intra-oral scanning device comprises a safety mechanism having an operating mode in which movement of the scanning arm is possible and a blocked mode in which movement of the scanning arm is prevented, wherein the safety mechanism is in the operating mode when the first mount structure of the main part is connected to the second mount structure of the mouthpiece and the safety mechanism is in the blocked mode when the first mount structure of the main part is not connected to any other structure. With such a safety mechanism, it can be achieved that the device can only be operated once it is fully functional. In particular, it can be prevented that the scanning arm is displaced while the mouthpiece is not connected to the main part and, thus, while the head portion is not covered and protected inside the mouthpiece.

Preferably, the at least one signal collector comprises a plurality of signal collectors. Such plurality of signal collectors may allow for providing a more accurate image. Additionally or alternatively, they can directly generate a three-dimensional image or a plurality of images at once. For example, from the plurality of images an appropriate computing unit, e.g. running an appropriate software, can generate a three-dimensional model.

Thereby, each of the plurality of signal collectors has afield of view with a view direction, wherein the view directions of the plurality of signal collectors are angulated in relation to each other. Such angulated arrangement of the view directions allows for efficiently providing a three dimensional image. Alternatively or additionally, it allows for providing a plurality of images of a single situation. From such plurality of images, information in plural dimensions can be derived.

Preferably, the scanning arm is equipped with a movement sensor. Such a movement sensor can comprise an accelerometer, a gyroscope or the like. It allows for detecting a movement of the arm, e.g., in relation to the main part. Like this, such relative movements may either be compensated automatically or scanning may be stopped until the relative movement is finished.

Preferably, the mouthpiece has a tapering section to suit into a mouth of a patient. Such tapering section allows the mouthpiece to be conveniently suited to the mouth of the patient. This allows for increasing comfort, acceptance and accuracy of the intra-oral scanning device.

Preferably, the main part comprises a programmable control unit for automatically and/or autonomously controlling the scanning arm and the at least one signal collector. Such control unit, which can be a computer or computing device, allows for automatically displacing the scanning arm and moving the at least one signal collector. In addition, it allows for evaluating the gathered data and to adjust or correct the further scanning operation. It also can reconstruct the data acquired such as scanned images to a model and particularly to a three dimensional model. This allows for a particular precise and convenient scanning operation. Furthermore, the control unit can comprise a storage such as a hard disk or the like for storing data acquired via the at least one signal collector. This can be advantageous in many applications, e.g., when the data cannot immediately be processed or forwarded for evaluation, display or the like.

Preferably, the drive mechanism comprises a tilt manipulator to which the scanning arm is mounted such that the scanning arm can be tilted. The tilting movement can be provided about the longitudinal axis of the scanning arm or an axis parallel to the longitudinal axis of the scanning arm. Alternatively or additionally, the tilt manipulator can tilt the scanning arm about other axis. Such a tilt manipulator allows for efficiently tilting the scanning arm and consequently the at least one signal collector. Like this, images around the teeth and jaws can be gathered and/or a three-dimensional image can be generated.

Preferably, the mouthpiece is provided with an identification code (ID). Such ID can be embodied as a QR-code, bar code, RFID or the like. It allows for identifying a specific mouthpiece. Thereby, e.g. it is possible to prevent reusing the same mouthpiece for different patients.

Preferably, the scanning arm is equipped with a light source. The light source can be or comprise a light emitting diode (LED) or the like. Such light source allows for efficiently illuminating the site inside the patient's mouth where the at least one scanner sensor performs scanning. Like this, the quality of the generated images can be improved. The light source may be embodied to emit light of a specific quality such as monochromatic light, polychromatic light, light of selected wavelengths and the like. Preferably, the signal collector or a sensing unit associated thereto is embodied in accordance with the specific light emitted by the light source.

Preferably, the main part is equipped with a display. Such a display can be embodied as a screen on which information can be shown. Alternatively, it might be a single or a set of lamps such as LED. By providing the main part with a display, it is possible to efficiently providing information about the intra-oral scanning device such as information about its status or the like.

Preferably, the intra-oral scanning device comprises a heater element arranged to heat the scanning arm, the head portion, the signal collector, the mouthpiece or any combination thereof. Such a heater element can allow for reducing possible fog appearing due to contact of plastic or other parts with humidity of the oral cavity. The heater element can heat the mentioned parts directly or indirectly, actively or passively. The heater element can be a computer or other electronic of the main part. The mouthpieces can be also pre-heated, e.g., in a station, before being used for a scanning process.

A further aspect of the invention relates to a scanner system comprising an intra-oral scanning device as described above and a plurality of mouthpieces of differing sizes. With such a scanner system, the effects and benefits described above in connection with the intra-oral scanning device and its preferred embodiments can efficiently be achieved. Furthermore, by providing plural mouthpieces in the system a suitable size can be chosen appropriate for a specific patient.

Preferably, the scanner system comprises an occlusion measurement plate adapted to identify a mouthpiece size suitable for a patient. It can comprise measurement sheets, e.g., made of paper. Such a measurement plate allows for precisely and quickly evaluating and selecting the appropriate size of mouthpiece for a patient. Thereby, the plate allows to measure the size of an arch of teeth which efficiently can be performed during occlusion or while the mouth is closed.

Preferably, the scanner system comprises a base station with a seat adapted to receive the main part of the intra-oral scanning device. Such base station can fulfil plural functions such as holding and storing the device, charging a battery of the device, generating a three-dimensional model of gathered data or images, or transferring data from the device.

Thereby, the main part of the intra-oral scanning device preferably is equipped with a battery and the base station has a charging structure adapted to charge the battery of the main part when being received in the seat of the base station. The charging structure can comprise a connector, which is connected to the main part for charging the battery. Alternatively, it can also be embodied for wireless charging of the battery.

Further, the main part of the intra-oral scanning device preferably is equipped with a data interface and the base station preferably has a corresponding data interface adapted to transfer scanning data from the data interface of the main part. The data interfaces can be universal serial bus (USB) interfaces. In such embodiments, the scanning data from the data interface of the main part is advantageously transferred when the main part is received in the seat of the base station.

Another further aspect of the invention relates to a method of operating an intra-oral scanning device as described above. The method comprises the steps of: mounting a mouthpiece of the intra-oral scanning device to the main part of the intra-oral scanning device; positioning the mouthpiece of the intra-oral scanning device in an oral cavity of a patient; identifying teeth in the oral cavity of the patient by moving an at least one signal collector on a head portion of a scanning arm of the intra-oral scanning device along a hollow interior of the mouthpiece of the intra-oral scanning device; calculating a scanning movement of the scanning arm of the intra-oral scanning device optimized for the identified teeth; and scanning the oral cavity of the patient by the scanning arm of the intra-oral scanning device performing the calculated scanning movement. Calculating the scanning movement and scanning the oral cavity can either be performed one after the other or simultaneously.

The term "scanning the oral cavity" in connection with the invention can relate to scanning essentially the complete oral cavity as well as scanning larger or smaller portions thereof such as scanning the palate or distal palate.

Such a method allows for an efficient and particularly accurate scanning of the oral cavity. Thereby, the complete process can be automatically performed.

Preferably, in the method an upper jaw of the patient and a lower jaw of the patient are moving relative to each other while at least part of the oral cavity of the patient is scanned. Like this, occlusion can be scanned or documented and analyzed. In this connection occlusion mean the contact between teeth particularly between teeth of the upper and lower jaw. More particularly, it can relate to the relationship between the maxillary (upper) and mandibular (lower) teeth when they approach each other, as occurs during chewing or at rest.

Preferably, when scanning the oral cavity of the patient, two-dimensional images are collected wherein a three dimensional model is generated from the collected two-dimensional images. This allows for a fast image collecting and scanning process.

Preferably, scanning the oral cavity of the patient is performed by the scanning device automatically and/or autonomously. Also, scanning the oral cavity of the patient preferably comprises collecting data about the geometry of the oral cavity of the patient and collecting data about the color of the oral cavity of the patient. Obtaining information about the geometry as well as about the color of the oral cavity or the jaw or teeth allows for improving the quality of the images or models generated. Also, the colors can be used for diagnostic purposes and for planning dental treatments.

BRIEF DESCRIPTION OF THE DRAWINGS

The intra-oral scanning device according to the invention, the scanner system according to the invention and the method according to the invention are described in more detail herein below by way of an exemplary embodiment and with reference to the attached drawings, in which.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs, which are not explained in the directly associated part of the description, then it is referred to previous or following description sections. Further, for reason of lucidity, if in a drawing not all features of a part are provided with reference signs it is referred to other drawings showing the same part.

Figure 1:
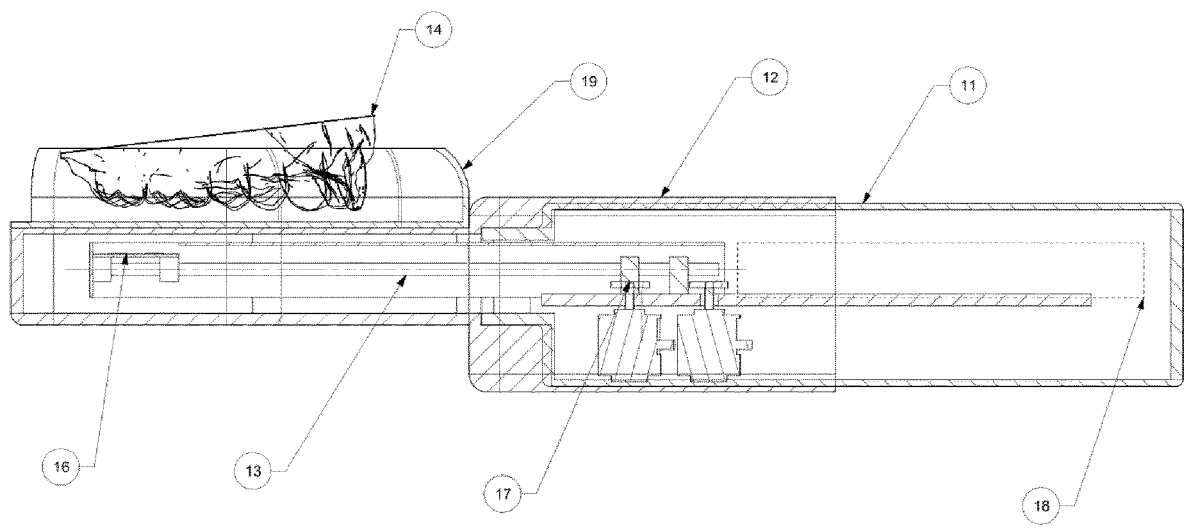
FIG. 1 shows a cross sectional side view of a first embodiment of an intra-oral scanning device according to the invention.

FIG. 1 shows a first embodiment of an intra oral scanning device according to the invention. It comprises a main part 11 and a mouthpiece 12 with a cover section to protect the main part 11. It further comprises a scanning arm 13, which in operation or while scanning protrudes from the main part 11 and extends out of the main part 11 into a hollow interior of the mouthpiece 12. As indicated with the dotted line the scanning arm can also be positioned inside the main part 11 in a parking position 18. There it is protected in the main part 11 and the mouthpiece 12 can be removed or replaced or the like.

At one longitudinal end, the scanning arm 13 has a head portion 16 that is equipped with plural scanning sensors as signal collectors and light sources. The mouthpiece 12 is positioned in the mouth of a patient such that an upper jaw 14 resides on a top surface of the mouthpiece 12. The mouthpiece 12 has a buccal wing portion 19 that is positioned between the cheek and the teeth of the upper jaw 14 of the patient. The wing portion 19 extends to and includes a proximal part of the oral cavity. Like this, a distance or free space between teeth and the cheek or the lips can be provided which allows for an improved scanning.

The intra-oral scanning device further comprises a drive mechanism with a pivot manipulator and a linear manipulator. In FIG. 1 the pivot manipulator is on the left-hand side and the linear manipulator is on the right-hand side. The pivot manipulator is arranged to pivot the scanning arm 13 about an axis of rotation 17.

Figure 2:
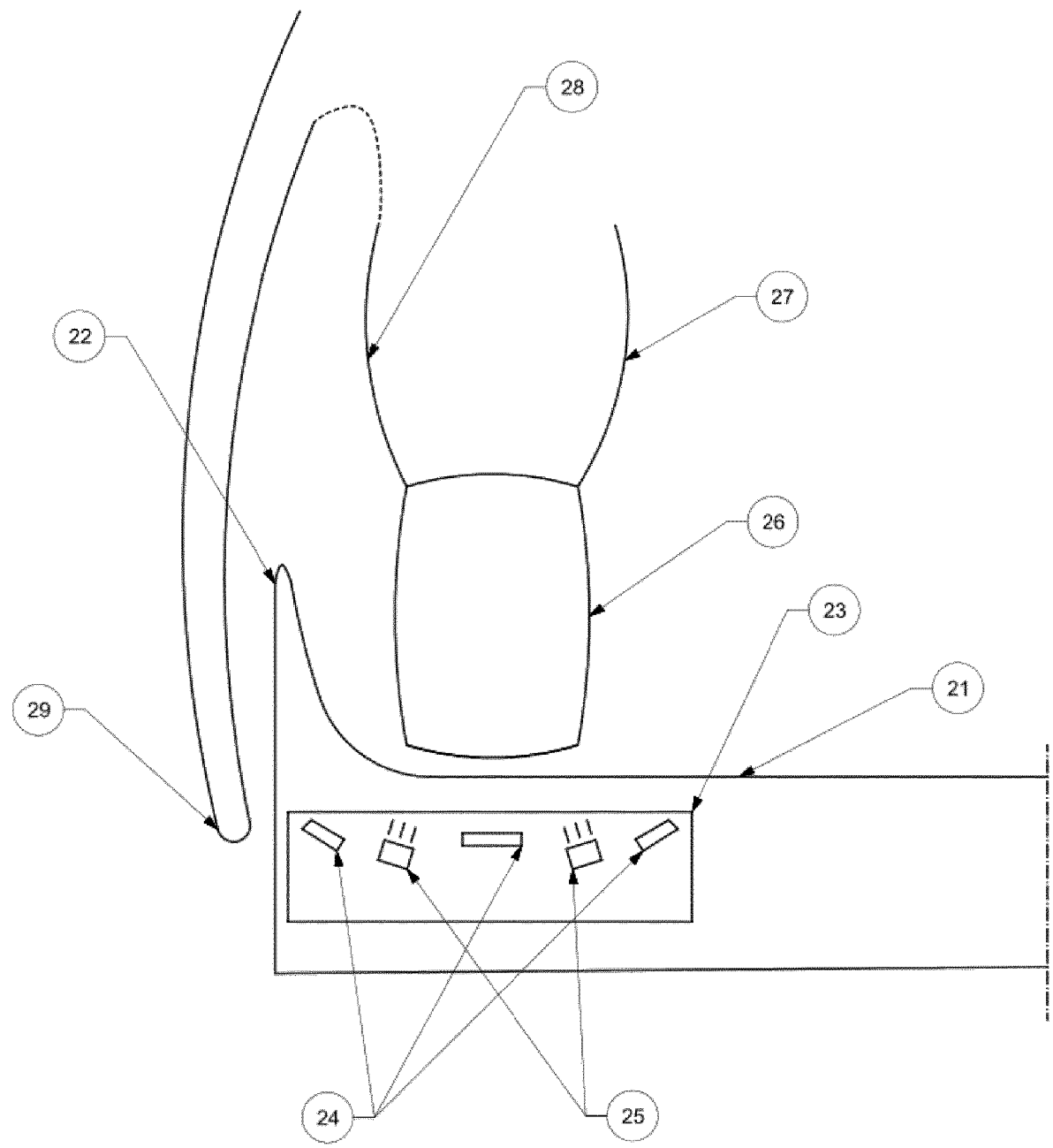
FIG. 2 shows a view of a head portion of a scanning arm of a second embodiment of an intra-oral scanning devoice according to the invention in operation.

In FIG. 2 a second embodiment of an intra-oral scanning device according to the invention is shown in operation. The device is similarly embodied as the first intra-oral scanning device described above. FIG. 2 shows a portion of a mouthpiece 21 arranged in an oral cavity of a patient below an upper jaw. The upper jaw comprises gingiva 27 and teeth 26, wherein the teeth 26 are adjacent to a transparent upper surface of the mouthpiece 21. The mouthpiece 21 has a wing portion 22 positioned between a vestibular side 28 of the gingiva 27 and a cheek 29 of the patient. By means of the wing portion 22, a distance or free space between the cheek 29 and a vestibular side of the upper jaw can be provided which allows for efficiently scanning the outer or vestibular side of the upper jaw as well.

A head portion 23 of a scanning arm of the second intra-oral scanning device is positioned inside a hollow interior of the mouthpiece and adjacent to the teeth 26 of the upper jaw. It is equipped with three scanning sensors 24 as signal collectors and two LED light sources 25. The light sources 25 are positioned in between each two neighbouring scanning sensors 24. Each of the scanning sensors 24 has a field of view in a predefined view direction wherein the view directions of the field of view are angulated towards each other. This is achieved by inwardly declining the left and right scanning sensors 24. In this way, a three dimensional image of the upper jaw can be generated by the three scanning sensors 24.

Figure 3:
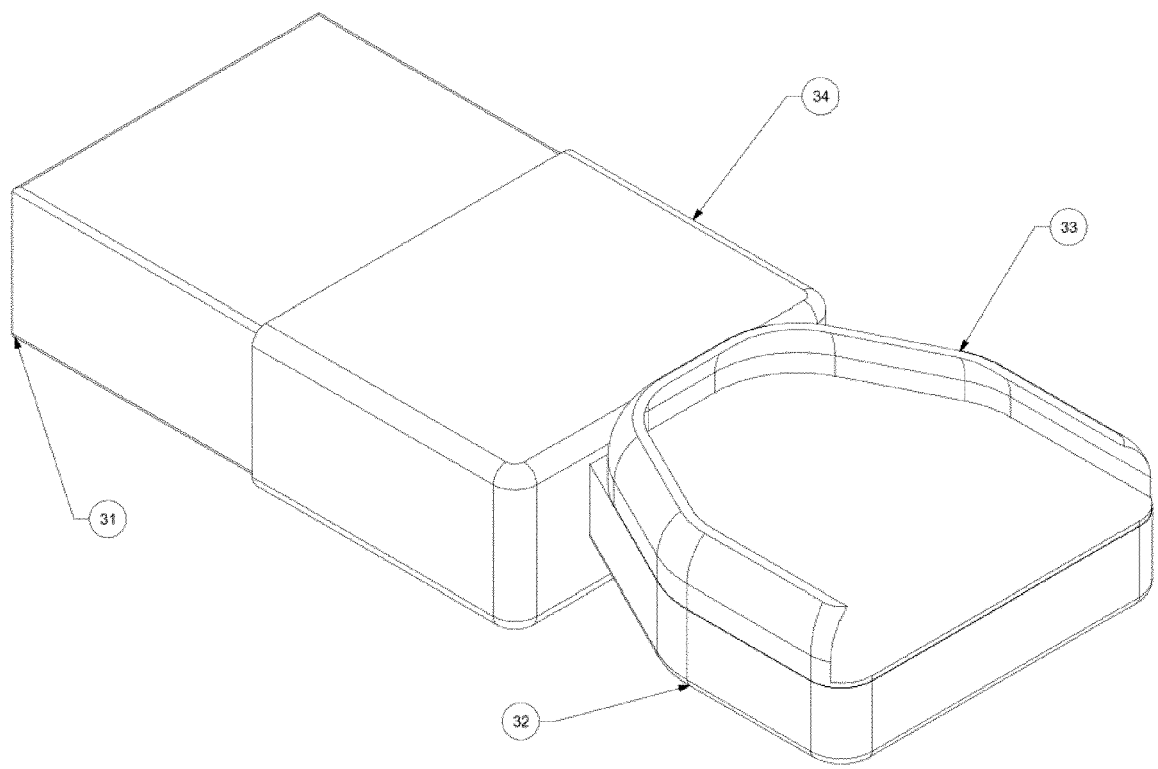
FIG. 3 shows a perspective view of a third embodiment of an intra-oral scanning device according to the invention.

FIG. 3 shows a third embodiment of an intra-oral scanning device. The device comprises a main part 31 and a mouthpiece 32, which has a wing portion 33. The main part 31 has a first mount structure and the mouthpiece 32 has a second mount structure 34. The first and second mount structures 34 are arranged to connect and release the mouthpiece 32 to and from the main part 31. In particular, the second mount structure 34 has a sleeve portion imposed over a section of the main part 31. Thereby, the sleeve portion on one hand holds the mouthpiece 32 on the main part 31 and on the other hand protects the main part 31 and particularly a transition between main part 31 and mouthpiece 32 where a scanning arm extends from the main part 31 into an interior of the mouthpiece 32.

Figure 4:
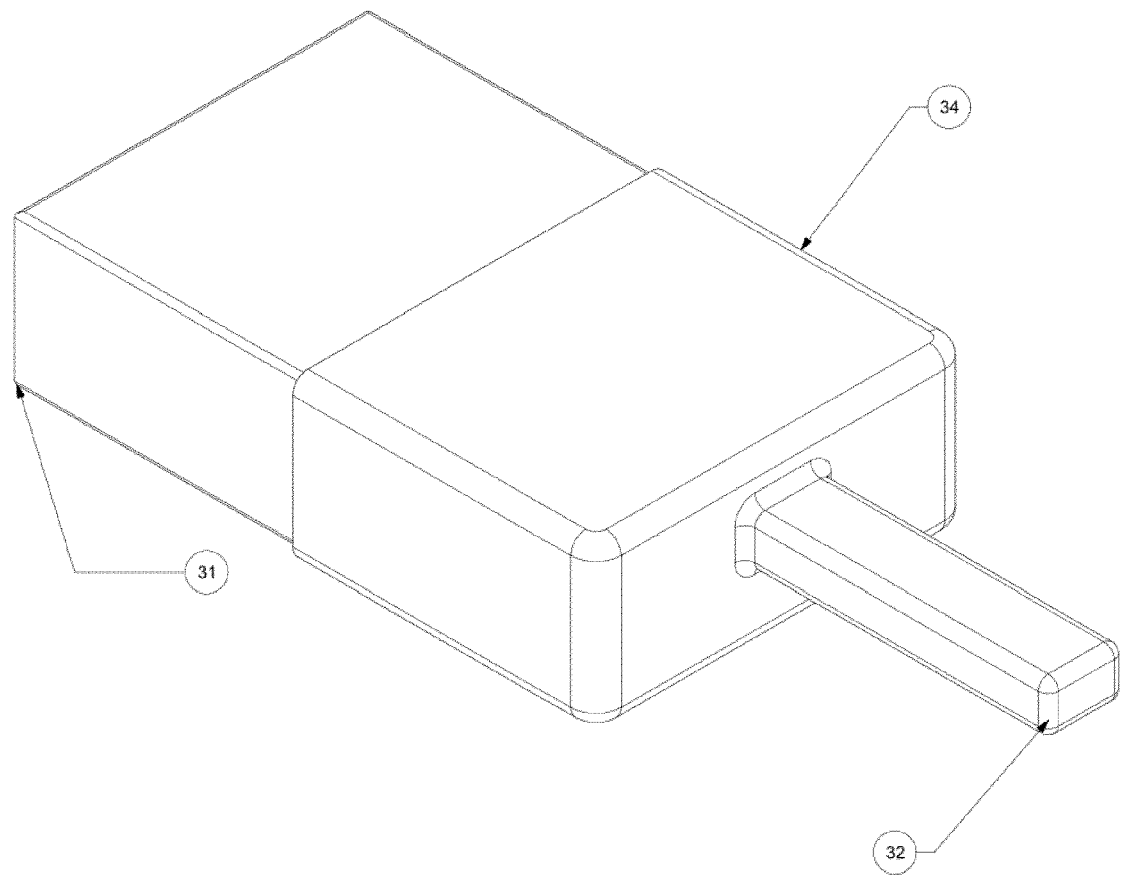
FIG. 4 shows a perspective view of a fourth embodiment of an intra-oral scanning device according to the invention.
Figure 5:
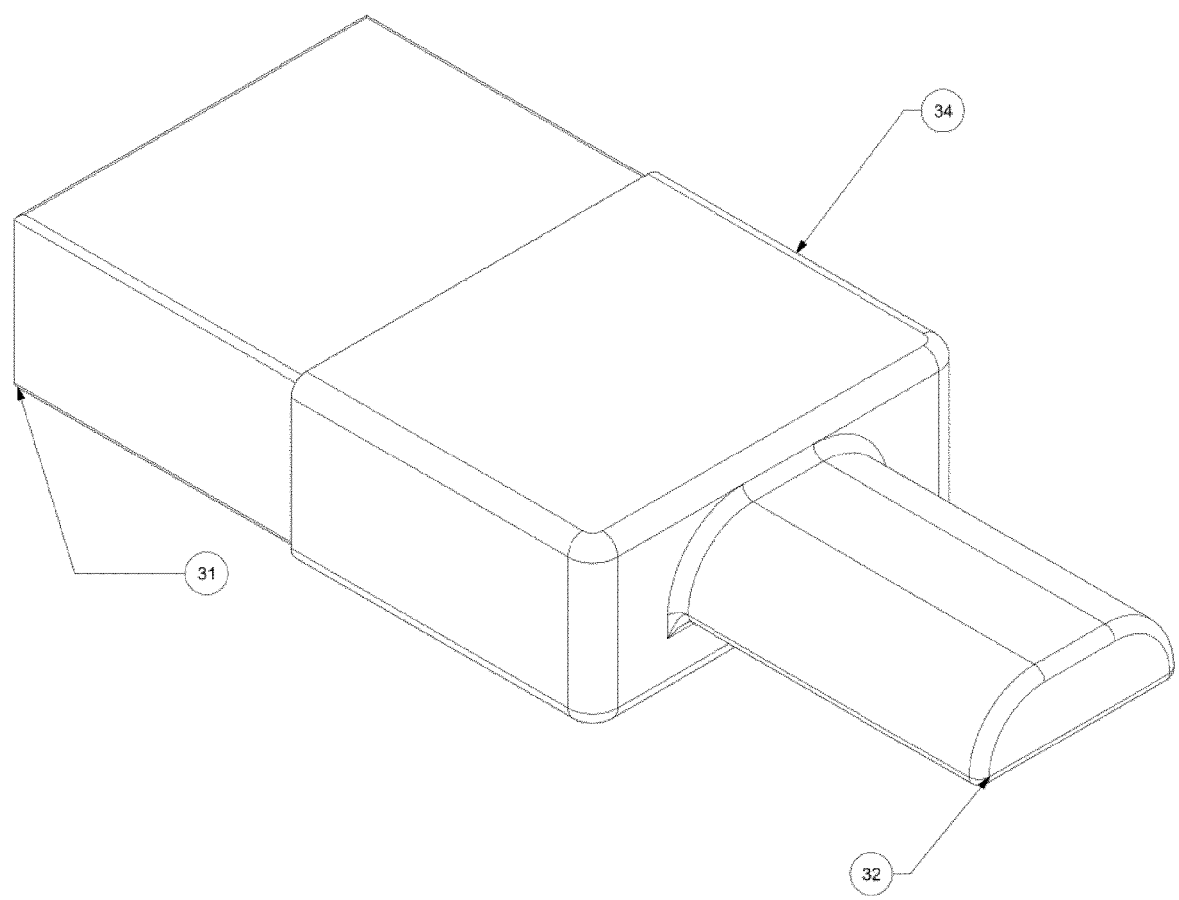
FIG. 5 shows a perspective view of a fifth embodiment of an intra-oral scanning device according to the invention.

In FIG. 4 and FIG. 5 a fourth embodiment and a fifth embodiment of intra-oral scanning devices are shown. The devices are identical to the intra-oral scanning device of FIG. 3, wherein the mouthpieces 32 are shaped differently. The mouthpieces 32 shown in FIGS. 4 and 5 are comparably slim. They are particularly shaped to be positioned in narrower zones of the oral cavity such as, specifically, between the cheek and the vestibular side of the upper and lower jaws, e.g., for an occlusal scanning.

Figure 6:
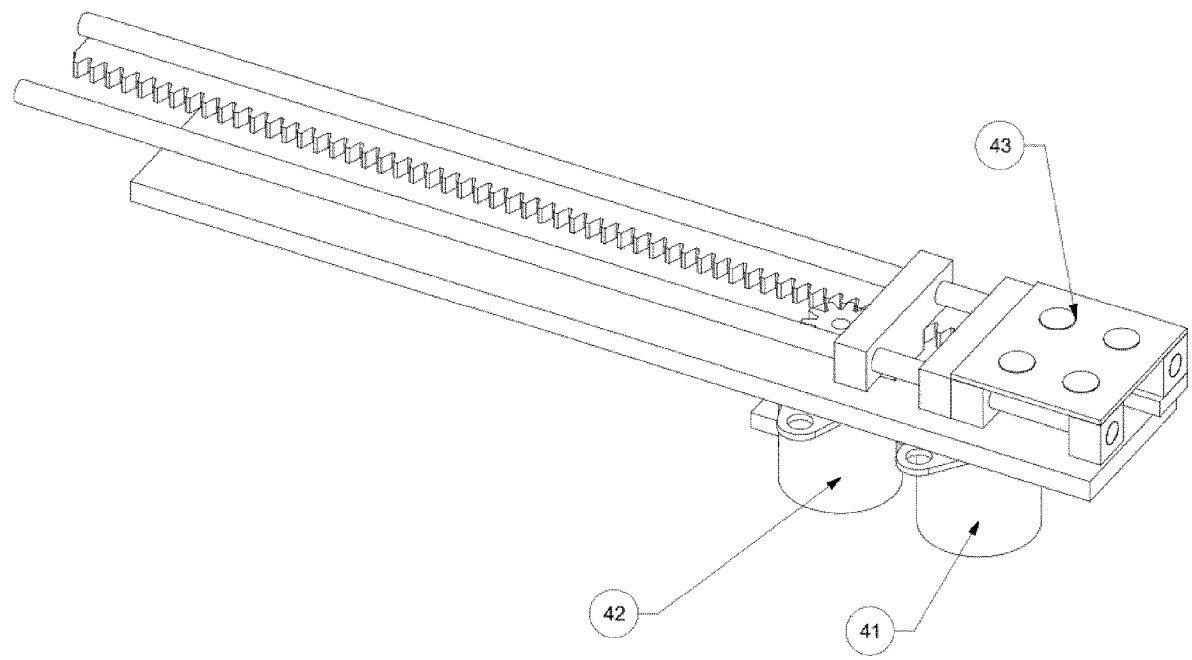
FIG. 6 shows a perspective view of a first embodiment of a drive mechanism of an intra-oral scanning device according to the invention.

FIG. 6 shows a first embodiment of a drive mechanism as it is suitable for all five embodiments of intra-oral scanning devices described above. It comprises a pivot manipulator 41, a linear manipulator 42 and a motor 43. The pivot manipulator 41 is embodied to pivot or rotate a scanning arm about an axis of rotation, which is perpendicular to a longitudinal axis of the scanning arm. It holds the scanning arm as well as the linear manipulator 42. The linear manipulator 41 is embodied to linearly move the scanning arm, i.e. moving along its longitudinal axis. The first drive mechanism allows for moving the head portion of the scanning arm in a polar coordinate system. This allows for a very robust and accurate movement wherein it a transition opening between main part and mouthpiece can be comparably small. This makes a flexible shaping of the mouthpiece possible. Particularly, the mouthpiece can be tapering towards the main part in order to suit into the mouth.

Figure 7:
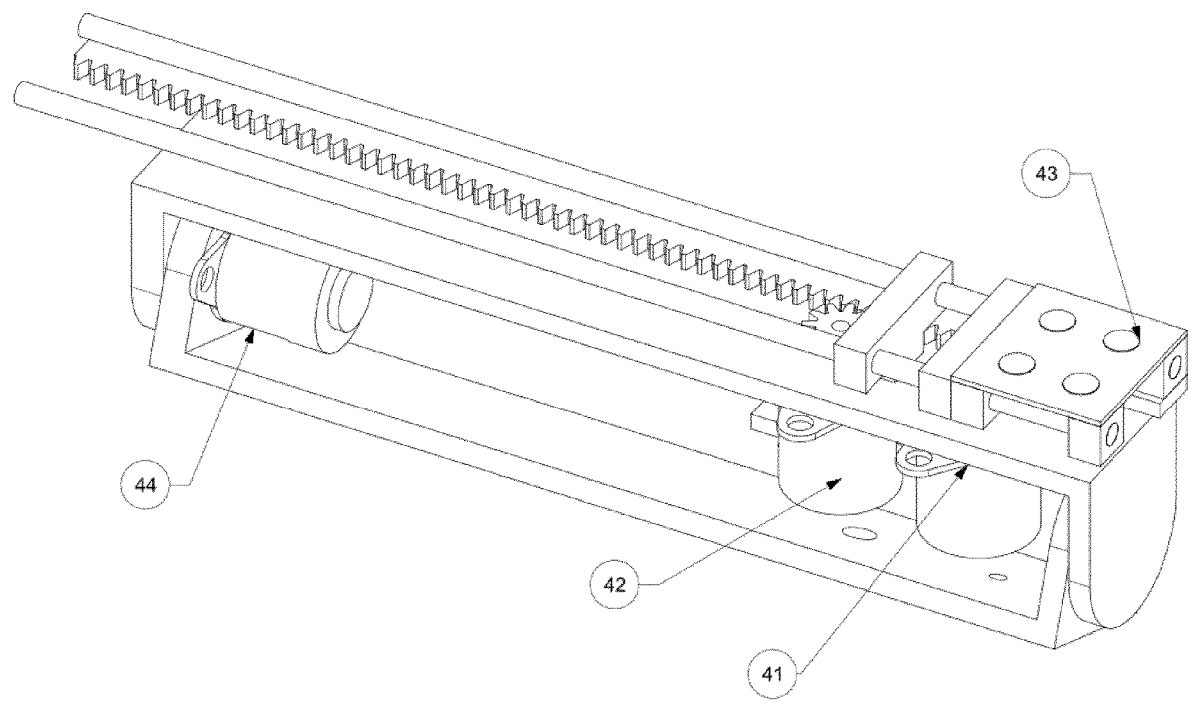
FIG. 7 shows a perspective view of a second embodiment of a drive mechanism of an intra-oral scanning device according to the invention.

In FIG. 7 a second embodiment of a drive mechanism is shown as it is suitable for all five embodiments of intra-oral scanning devices described above. It comprises a pivot manipulator 41, a linear manipulator 42 and a motor 43 identical to the respective parts of the first drive mechanism. Additionally, the second drive mechanism has a tilt manipulator 44. The tilt manipulator 44 is embodied to hold and tilt the pivot manipulator 41, the linear manipulator 42 and the scanning arm together. Like this, scanning arm and particularly its head portion can be tilted about an axis parallel to the longitudinal axis of the scanning arm.

Figure 8:
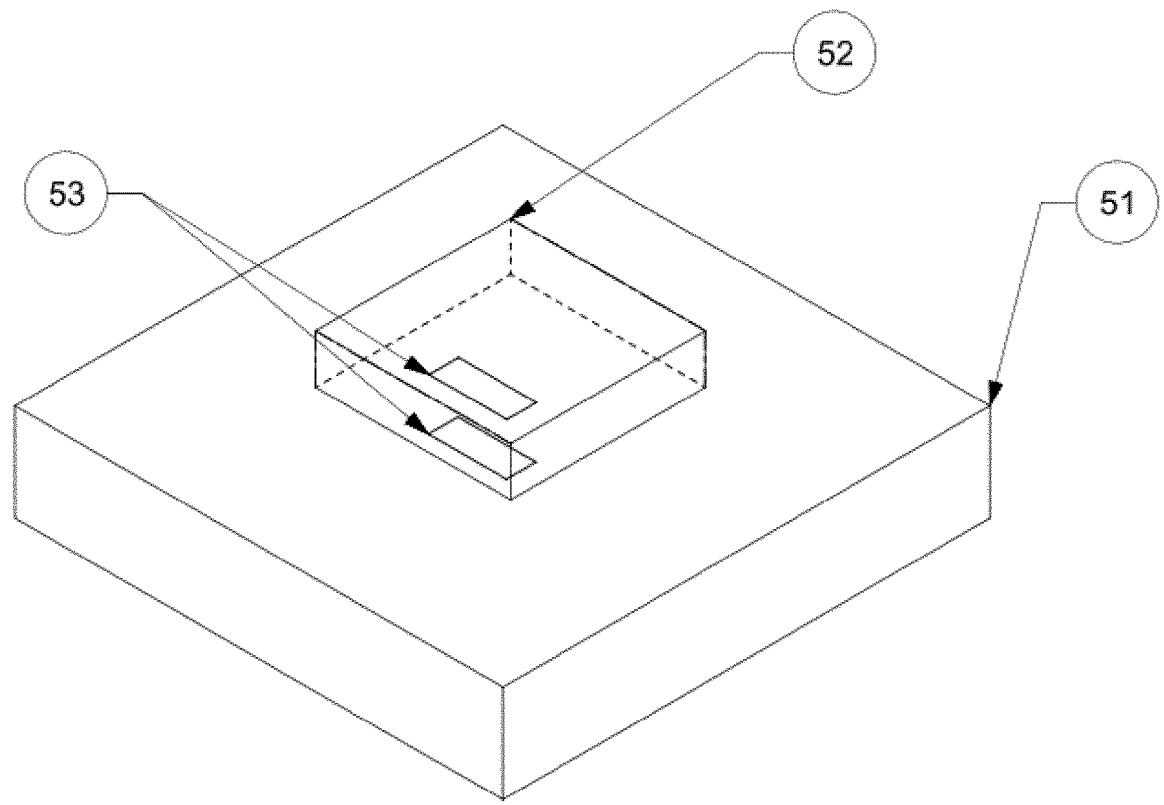
FIG. 8 shows a perspective view of a base station of an embodiment of a scanner system according to the invention.

FIG. 8 shows a base station 51 of an embodiment of a scanner system according to the invention. The scanner system also comprises an intra-oral scanning device, e.g., one as it is described above or similar. The base station 51 has a seat receiving a main part 52 of the intra-oral scanning device. The main part 52 is equipped with a battery as energy source and a charging antenna 53. The base station 51 has a corresponding charging antenna 53. When the main part 51 is received in the seat of the base station 51 the battery can be charged via the antennas 53.

Base stations in accordance with the present disclosure such as the one shown in FIG. 8 can comprise a chassis, a power charger, a battery and a connector such as a USB 3.0 connector. The power charger can be used to charge the intra-oral scanning device and the battery of the base station. The battery is to be used when there is a power loss or instability in the location of using the device or when the system is used outdoor. The USB 3.0 connector can have a male plug to cooperate with a female socket from the main part of the intra-oral scanning device. An embedded software can be executed in the base station to control functions of the system.

The base station can also be an alternative computer, e.g., to do a reconstruction of the 3D structure of teeth and gingiva based on the images transferred from the main part of the intra-oral scanning device. Alternatively, this can be done directly by a computer or control unit of the main part. The computer of the base station can also be used to inspect the data or if a 3D model is reconstructed by the main part, which can be referred to as the stl-file. The stl-file can be sent directly to a computer of a user such as a tablet, a smartphone or a computer into the cloud or the Internet.

Figure 9:
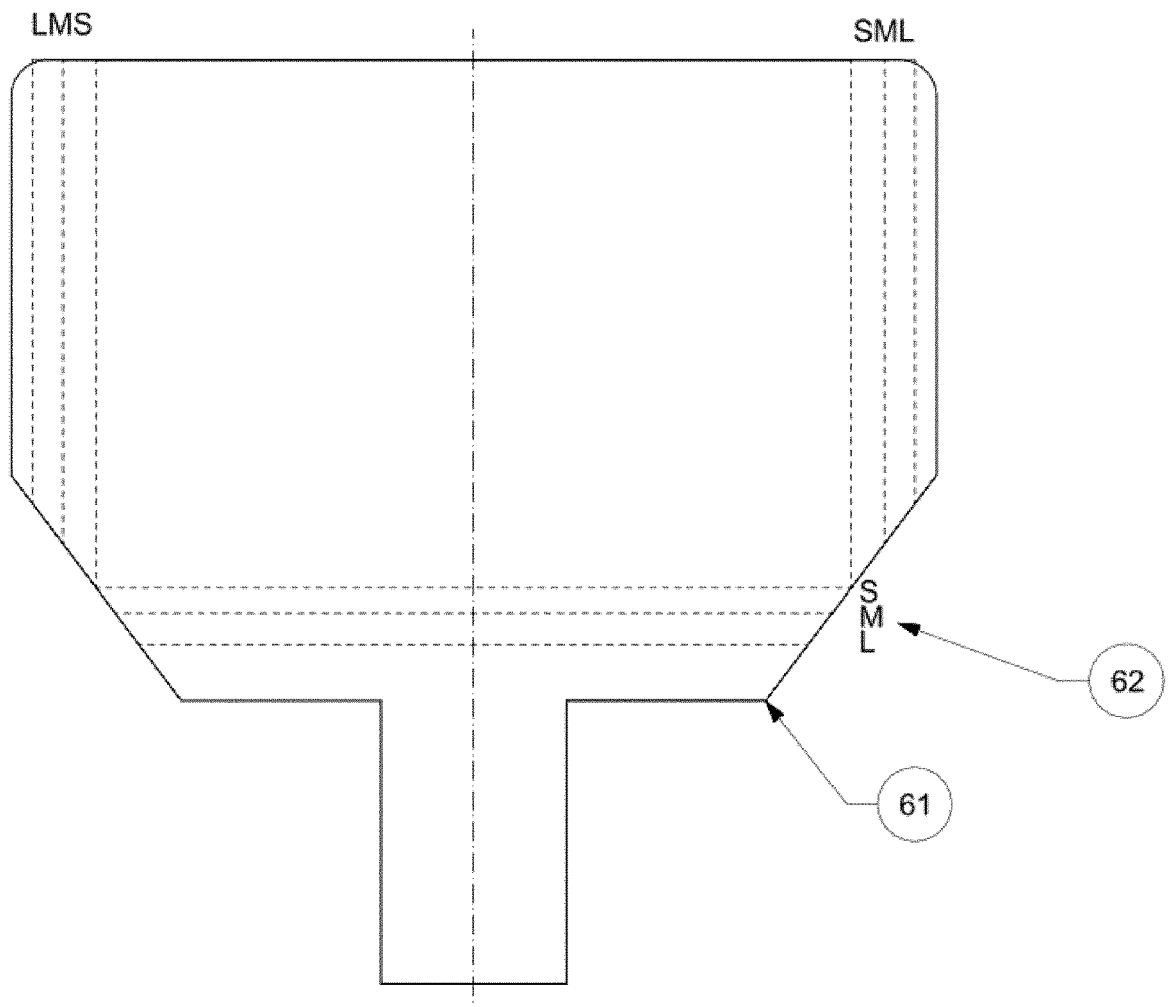
FIG. 9 shows a top view of an occlusion measurement plate of the scanner system of FIG. 8.

In FIG. 9 an occlusal measurement plate 61 of the scanner system is shown. The measurement plate 61 has a gripping portion and a main portion. In use, the gripping portion is held and the main portion is positioned in the oral cavity of a patient. The main portion is further provided with scale markings 62, which allow depicting a size of a mouthpiece suitable for the specific oral cavity.

Thus, the occlusal measurement plate 61 can measure the size of the oral cavity. It can comprise a block of paper, made with repellent paper, either impregnated or being made with tracing paper like. Each paper sheet can have a scale drawn on both sites. An operator or the patient himself will dispose one sheet into the oral cavity and the patient by biting it marks the size of the jaw. Based on marks from the teeth on the paper, the operator can select the proper size of the mouthpiece to be used.

The scanner system can also comprise a carrying case. It can be made of a material, which has given industrial design and mechanical shape to be able to house a foam like or cartoon like material inside with wholes adjusted to keep tight the intra-oral scanning device and the main part.

Figure 10:
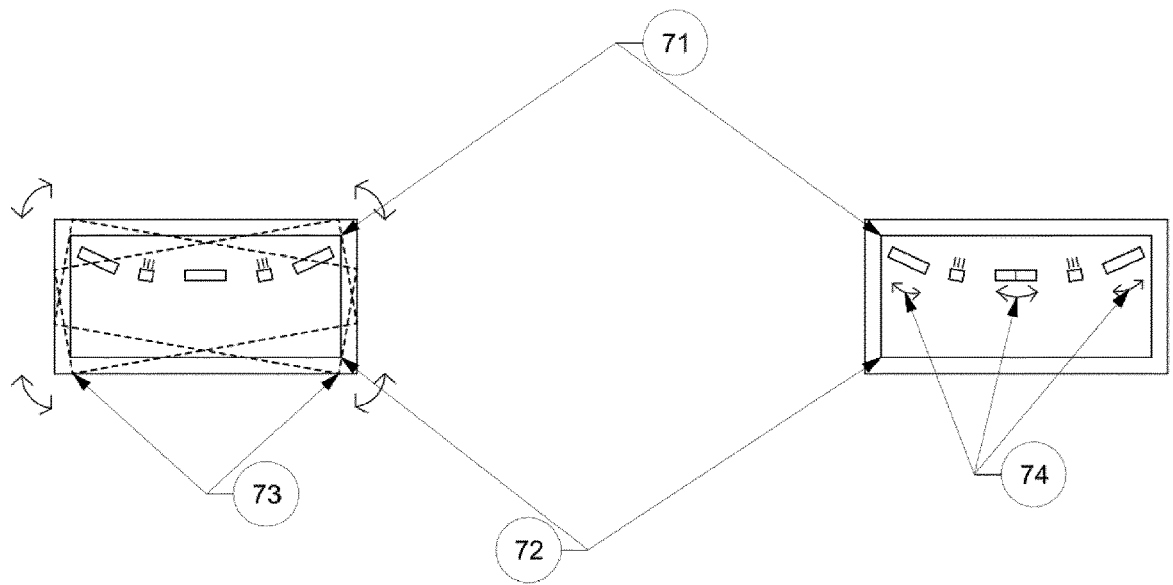
FIG. 10 shows two versions of tilting movements of scanning sensors in operation.

FIG. 10 shows two ways of tilting operation within an oral scanning process. In a first way, in FIG. 10 this is illustrated on the left-hand side, a complete head section 72 of a scanning arm of an intra-oral scanning device 71 is tilted. Such tilting can either be performed manually or by an automatic mechanism, i.e. by means of a drive mechanism. Like this, varying tilting positons 73 of the head section 72 can be achieved which may allow to generate an accurate three-dimensional image of the intra oral cavity.

In a second way, in FIG. 10 this is illustrated on the right-hand side, single scanning sensors 74 as signal collectors of the head portion 72 are tilted individually by the drive mechanism. This allows for a particular sophisticated image generation.

Figure 11:
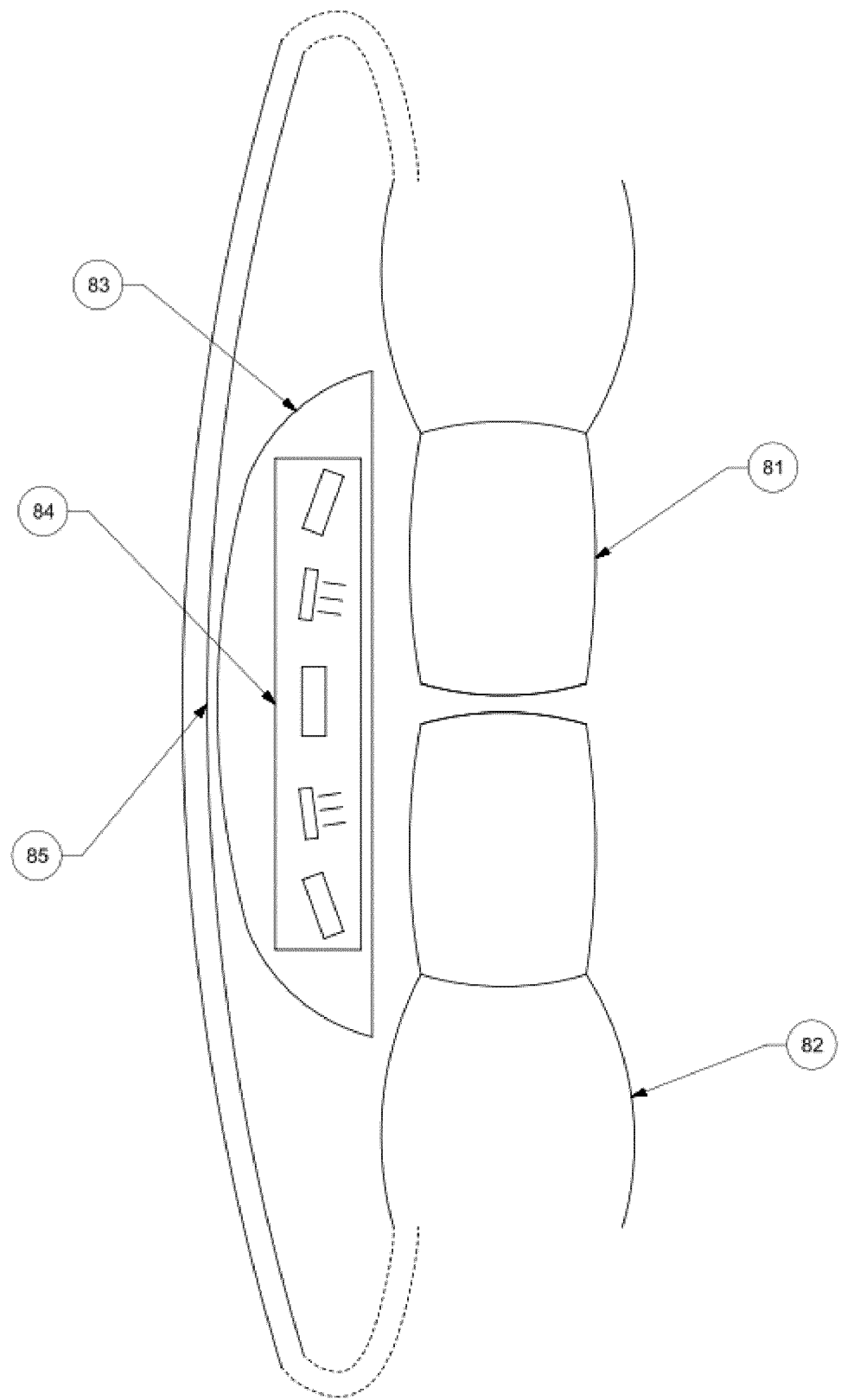
FIG. 11 shows a view of the intra-oral scanning device of FIG. 5 in operation.

In FIG. 11 a scanning process is shown in which the occlusion and dynamic occlusion of an oral cavity is scanned. For that purpose, an intra-oral scanning device similar to the one shown in FIG. 5 is used. A mouthpiece 83 of the scanning device is positioned at a vestibular side of an upper jaw 81 and a lower jaw 82 between the jaws and a cheek 85. A head portion 84 of a scanning arm is then moved along the jaws 81, 82 and scanning sensors thereof as signal collectors generate images of the jaws 81, 82. Thereby, the upper jaw 81 and the lower jaw 82 may be moved in relation to each other such that the dynamics of the jaws can be gathered and analysed.

Intra-oral scanning devices as exemplified by the embodiments and as described above in connection with the invention can be controlled using a dedicated advanced software, which supports using the device, service and maintenance. One function of the software can be to execute the acquisition of images and reconstruct the 3D structure of the oral cavity.

In the following features, functions, operations and properties of embodiments of the intra-oral scanning device according to the invention, the scanner system according to the invention and the method according to the invention are described which may be implemented individually or in any possible combination.

General performance of the intra-oral scanning devices is based on a "no button" principle. The main part after attaching the mouthpiece needs to be positioned in a patient's mouth and all scanning process will be carried automatically, e.g., until on a display a stl file with the 3D model of the oral cavity appears. The patient can be a living or dead human or animal being as well as a model of those, an archaeological artefact or the like.

The disclosed intra-oral scanning devices can have the purpose of performing an autonomous scanning of a patient's mouth, however also automatic mode can give significant advantage. A semi-automatic and manual scanning mode may be used as well but preferably for research purposes and for using the device in special clinical use in non-standard cases.

In the automatic scanning mode, the intra-oral scanning device can have following working functions: 1. means to connect the device, e.g., by WIFI into the base station and/or computer from a user, or connected, e.g., via USB 3.0 when the main part is connected to the base station. 2. Adjusting the device performance based on identification of the connected mouthpiece. The size of the mouthpiece may influence the range of movement predefined for the scanning arm. 3. A scout view can be executed by doing a defined moving pattern around the mouthpiece using reduced resolution of the images with optional life view on the user's computer. 4. An acquisition view can be executed similarly as in step 3 but using movement path definitions obtained in step 3, at slower speed and maximum required resolution for the images.

In the semi-automatic scanning mode a scanning process can be executed which is controlled by the operator. The user or operator can select the location where the scanning device needs to move as well as define the path, which the head portion is to travel and to acquire images. This can be done by a user-friendly software application, which shows the visualisation of the scanning arm position during scanning. This mode can be able to be used by advanced users to test individual procedures before they are stored in an automatic mode for using by all users.

The manual scanning mode can be used like the semi-automatic mode but instead of selecting the point in the application, the user inputs the number of steps to linear movements and angels of rotation to execute the movement of the scanning arm. This mode can be used by engineers to test the performance of the scanning device within the custom designed mouthpiece and also during service maintenance.

In the autonomous scanning mode, the intra-oral scanning device can be operated at least in two variants. (i) Autonomous, based on a list of rules is not any automatic pattern for arm movement stored, instead the scanning device works based on the list of rules formulated as a typical behaviour of the scanning device. If comparing the scanning device to transportation systems, the automatic mode works like a tram which has own strictly defined path, while autonomous mode works like a taxi, when starting and end point and trained cap driver is deciding how car should be drive. In the autonomous mode, scanning device may have several rules: 1. Rules based on identification of the mouthpiece, the boundary of movement are defined. E.g., the scanning device never forces the scanning arm to move further than the mouthpiece boundary. 2. The scout view is executed to identify a proper path for the major scanning step. 3. When the scanning arm starts to work and drives out from the main part, images are taken continuously and a software analyses the features appearing on the images. 4. If a tooth is identified on the screen, the scanning arm tries to position the tooth in the middle of the image, and next travels to right site of the tooth. Every time when the tooth is moved out of the centre view there is a correction of the scanning arm position applied. In this way, the scanning arm can follow the tooth until end of arch on the right site. 5. A similar procedure is taken during moving of scanning arm to a left site of the arch. 6. Based on the arch geometry autonomous identification of the path for acquisition view is defined. 7. As a next step an acquisition view is executed. 8. At the end the scanning arm returns back to the parking position in the main part.

The whole process can be applied even for teeth in very not standard arch and it can be created by the scanner itself with no operator influence.

(ii) Autonomous based on auto learning algorithms mode: in this mode, the scanning device can use knowledge from previous scans executed using in other modes. The arch for the scout view can be taken from already accomplished scans when the same size of mouthpiece was used. The scout view from previous scans can be used to define the path or average path can be calculated based on a previous use of scanner. The system during acquiring view a monitor position of the tooth on images and if case path can be not correct, apply corrections into the scanning arm movement. Before this mode can be possible to use the learning procedure can be required to be executed. It could be able to do based on early studies as each scan has information about path stored in the designated file.

The intra oral scanning devices disclosed may have the following functioning: A standard automatic scan in which, after removing the intra-oral scanning device from the carrying case, the base station can be connect to a user's PC by USB 3.0. The main part of the device can be stored on the base station and charging can be executed if required.

Using the occlusion measurement plate to measure the size of the oral cavity the actual size of the oral cavity can be measured. The operator can take one sheet of paper and deposing it to the oral cavity. After biting it, the shape of the teeth's can be marked on the paper. The size of oral cavity is, e.g., estimated as a L. The envelope with mark L can be opened in front of the patient and clean mouthpiece can be taken out from envelop and attached to the main part of device.

The intra oral scanning device, since the mouthpiece is mounted, can do identification check by scanning the QRcode located on the mouthpiece. The scanned ID of mouthpiece can be sent to a database to download the information about mouthpiece. If the verification of the data is positive the mouthpiece was not used before and a series information has been successfully downloaded.

The patient can then be asked to bite the mouthpiece and keep it in one position until progress bar showing a progress of scanning on the user computer screen will be full and a voice signal can be executed. The patient can position the mouthpiece inside the oral cavity between upper and lower tooth and in position down into the $8^{th}$ molars and bites it with small force.

The intra oral scanning device can monitor the acceleration of the scanner, which is stable in Z direction when the device is properly held in the patient's mouth. After this happened the device can emit a signal and/or green light to show the position has been fixed. On the user screen, the progress bar for the scan can be shown.

The mouthpiece can maintain the scanner position in the oral cavity in place where scanning needs to be executed. Depending on the type of mouthpiece and head portion of the scanning arm, it can be either both upper and lower tooth, one tooth arch or part of the tooth like at least part of the tooth.

After the intra-oral scanning device identified its fixed position inside the oral cavity, the scanning arm can move out from the main part and being housed inside the mouthpiece. It can safety penetrate the cavity by traveling around mouthpiece and have no contact with patient's tissue or liquid. The scanning arm can be separated and protected by the disposable mouthpiece. The mouthpiece can provide space for the scanning arm and in the same time protects the patient's mouth from being hurt by the scanning arm. The scanning arm can travel around the oral cavity without any contact with tissue as well as the mouthpiece. It can be moved and optionally tilted by the motor and driving mechanism operated in the main part in a polar coordinate system and by other motor operated there in a linear coordinate system.

During scanning, light is emitted by LED light sources located in the head portion of the scanning arm. The light can be propagated through the translucent material of the window in the head portion and the mouthpiece into the oral cavity lighting the 3D structure of teeth, implants, gap with not tooth and gingiva. At the same time, the mentioned 3D structure can be observed by the scanning sensors as signal collectors located in the head portion. Cameras or the scanning sensors may acquire a collection of 2D images and send them to the main part.

The main function of the intra-oral scanning device may be executed as follows: A scanning function starts from the main part, where the scanning arm is positioned in a parking position taken after finishing earlier work. The scanning arm is doing the scout view. The scanning arm is travelling from the main part into the mouthpiece to the right site of the patient mouth in rear location. Movement of the scanning arm is executed by proper adjustment of the pivot manipulator to rotate the arm into right site and linear manipulator to move the end portion of the scanning arm in to the rear corner of the mouthpiece. Next, the scanning arm is moved from right rear position into the front right position in the mouthpiece, next the scanning arm be moved to the front left position and next into the left rear position. During movement of the scanning arm, the head portion is acquiring the images, which will be analysed by a software to see if the path of arm movement is properly adjusted into the tooth arch. If a line of teeth does not appear on the images, the path is corrected and with new traction, the scout view is repeated. The scout view also allows adjustment of proper illumination, required to get a high quality images during major scan. It also enables the test of quality of the either mouthpiece, if fog appear on scanning head window or mouthpiece, the heating is executed to reduce the fog.

As a result, from the scout view the path of moving the scanning arm and acquiring parameters for cameras and illumination system is obtained. The whole scout view can take about six seconds.

After the scout view is finished, the acquiring view is executed. The scanning arm is moved by the drive mechanism in a defined speed along the path obtained as a result of scout view. During moving the scanning arm, other parameters of acquisition like settings for the cameras and light are also used and scanning head is acquiring high-resolution images. The whole acquisition view can take about three seconds and may be quicker than the scout view.

During all acquisition time the scanner system can monitor the signal from an accelerometer as well as from image processing, if they inform about rapid move of the mouthpiece, the scan can be repeated. This prevents the device from providing imaging data with low quality.

After the acquisition view, the scanning arm can return back into the parking position inside the main part. A door in the main part can close automatically. In the mean time, the reconstruction of the 3D structure of teeth and gingiva can be carried out on the computer or control unit in the main part and effect of this reconstruction in form of a stl-file is sent by WIFI to the user's computer. Both operator and user can see the image of the model on the screen shown with use of dedicated application. Next, the diagnosis and treatment can be carried out with high precision based on the model which represents the three-dimensional geometry including colors of the oral cavity.

The disclosed intra-oral scanning device and scanner system can be used in medical applications such as orthodontic, prosthesis, implants, inter-channel treatment, periodontology, archive of beauty teeth, tracking of the dynamic occlusion, palatum defect, submucous cleft palate, screening and monitoring of carries and screening for cancer applications. Other applications may be autonomous scan, occlusion scan, occlusion dynamic scan and child scanning (no rotated movement) applications.

Using results of the scanning process carried out by the intra-oral scanning device can include: using 3D geometry of teeth and gingiva, e.g., in form of either point cloud, including texture, or stl, including coloured stl, for designing intra-channel inserts or prosthesis such as crowns, inlays or onlays, based on stl; diagnosis of condition of tooth before designing of orthodontic treatment and later design of shape of the wire and position of braces, or retainer; making digital impression for non-medical use (non diagnostic function); and scanning of 3D tooth and gingiva shape and make the rubber protector for football and hockey players.

This description and the accompanying drawings that illustrate aspects and embodiments of the present invention should not be taken as limiting-the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims.

The present disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. An intra-oral scanning device, comprising:
a main part having a first mount structure;
a scanning arm having a head portion equipped with at least one signal collector, wherein the scanning arm is mounted to the main part and is arrangeable to protrude from the main part;
a drive mechanism connected to the scanning arm to move the head portion of the scanning arm along an oral cavity of the patient; and
a mouthpiece for being positioned in the oral cavity of a patient, the mouthpiece having a hollow interior, an opening to access the hollow interior and a second mount structure corresponding to the first mount structure of the main part, wherein the scanning arm extends into the hollow interior of the mouthpiece when the first mount structure of the main part is connected to the second mount structure of the mouthpiece,
wherein
the drive mechanism has a pivot manipulator and a linear manipulator,
the scanning arm is mounted to the pivot manipulator such that an axis of rotation of the pivot manipulator is essentially perpendicular to a longitudinal axis of the scanning arm, and
the scanning arm is mounted to the linear manipulator such that a distance between the pivot manipulator and the head portion of the scanning arm is modifiable.

2. The intra-oral scanning device of claim 1, wherein
the drive mechanism has a motor arrangement arranged to adapt the pivot manipulator and the linear manipulator in order to move the head portion of the scanning arm in the hollow interior of the mouthpiece, and/or
the mouthpiece is made of a disposable material, and/or
the mouthpiece has a top portion limiting the hollow interior and arranged to be directed towards an upper jaw of the patient when the mouthpiece is positioned in the oral cavity of the patient, the top portion being made of a transparent material.

3. The intra-oral scanning device of claim 1, wherein the mouthpiece has a bottom portion limiting the hollow interior and arranged to be directed towards a lower jaw of the patient when the mouthpiece is positioned in the oral cavity of the patient, the bottom portion being made of a transparent material.

4. The intra-oral scanning device of claim 3, wherein the at least one signal collector is arranged to simultaneously scan via a top portion of the mouthpiece and the bottom portion of the mouthpiece when the head portion of the scanning arm is arranged inside the hollow interior of the mouthpiece.

5. The intra-oral scanning device of claim 1, wherein the scanning arm is exclusively movable by the pivot manipulator rotating the scanner arm about the axis of rotation and the linear manipulator moving the scanner arm along its longitudinal axis.

6. The intra-oral scanning device of claim 1, wherein the pivot manipulator of the drive mechanism is mounted to the main part and the linear manipulator of the drive mechanism is mounted to the pivot manipulator of the drive mechanism.

7. The intra-oral scanning device of claim 1, wherein the mouthpiece comprises a sideward and/or frontward extending wing portion arrangeable between soft tissue of the patient and a jaw of the patient when the mouthpiece is positioned in the oral cavity of the patient.

8. The intra-oral scanning device of claim 1, wherein the mouthpiece comprises a frontward extending shield portion arrangeable adjacent to the main body in front of the mouth of the patient when the mouthpiece is positioned in the oral cavity of the patient, and/or
the intra-oral scanning device further comprises a data interface for transferring scanner data gathered via the at least one signal collector,
wherein the data interface preferably is a wireless data interface, and
wherein the data interface is arranged to transfer data gathered by the at least one signal collector to a remote computer or a remote display.

9. The intra-oral scanning device of claim 1, comprising a safety mechanism having an operating mode in which movement of the scanning arm is possible and a blocked mode in which movement of the scanning arm is prevented, wherein the safety mechanism is in the operating mode when the first mount structure of the main part is connected to the second mount structure of the mouthpiece and the safety mechanism is in the blocked mode when the first mount structure of the main part is not connected to any other structure.

10. The intra-oral scanning device of claim 1, wherein
the at least one signal collector comprises a plurality of signal collectors, and
each of the plurality of signal collectors has a field of view with a view direction, wherein the view directions of the plurality of signal collectors are angulated in relation to each other.

11. The intra-oral scanning device of claim 1, wherein the scanning arm is equipped with a movement sensor.

12. The intra-oral scanning device of claim 1, wherein
the mouthpiece has a tapering section to suit a mouth of a patient, and/or
the main part comprises a programmable control unit for automatically and/or autonomously controlling the scanning arm and the at least one signal collector, and/or
the drive mechanism comprises a tilt manipulator to which the scanning arm is mounted such that the scanning arm can be tilted.

13. The intra-oral scanning device of claim 1, wherein the mouthpiece is provided with an identification code.

14. The intra-oral scanning device of claim 1, wherein
the scanning arm is equipped with a light source, and/or
the main part is equipped with a display, and/or
the intra-oral scanning device further comprises a heater element arranged to heat the scanning arm, the head portion, the signal collector, the mouthpiece or any combination thereof.

15. The intra-oral scanning device of claim 1, wherein the at least one signal collector comprises a scanning sensor.

16. A scanner system comprising:
an intra-oral scanning device according to claim 1; and a plurality of mouthpieces of differing sizes, and, optionally,
an occlusion measurement plate adapted to identify a mouthpiece size suitable for a patient.

17. The scanner system of claim 16, further comprising a base station with a seat adapted to receive the main part of the intra-oral scanning device,
wherein
the main part of the intra-oral scanning device preferably is equipped with a battery and the base station has a charging structure adapted to charge the battery of the main part when being received in the seat of the base station, and/or
the main part of the intra-oral scanning device preferably is equipped with a data interface and the base station has a corresponding data interface adapted to transfer scanning data from the data interface of the main part.

18. A method of operating an intra-oral scanning device according to claim 1, comprising:
mounting a mouthpiece of the intra-oral scanning device to a main part of the intra-oral scanning device;
positioning the mouthpiece of the intra-oral scanning device in an oral cavity of a patient;
identifying teeth in the oral cavity of the patient by moving at least one signal collector on a head portion of a scanning arm of the intra-oral scanning device along a hollow interior of the mouthpiece of the intra-oral scanning device;
calculating a scanning movement of the scanning arm of the intra-oral scanning device optimized for the identified teeth; and
scanning the oral cavity of the patient by the scanning arm of the intra-oral scanning device performing the calculated scanning movement.

19. The method of claim 18, wherein an upper jaw of the patient and a lower jaw of the patient are moving relative to each other while at least part of the oral cavity of the patient is scanned.

20. The method of claim 18, wherein when scanning the oral cavity of the patient two-dimensional images are collected whereby a three-dimensional model is generated from the collected two-dimensional images, and/or
scanning the oral cavity of the patient is performed by the scanning device automatically and/or autonomously, and/or
scanning the oral cavity of the patient comprises collecting data about a geometry of the oral cavity of the patient and collecting data about a color of the oral cavity of the patient.

* * * * *